United States Patent [19]
Davis et al.

[11] Patent Number: 5,185,440
[45] Date of Patent: Feb. 9, 1993

[54] CDNA CLONE CODING FOR VENEZUELAN EQUINE ENCEPHALITIS VIRUS AND ATTENUATING MUTATIONS THEREOF

[75] Inventors: Nancy L. Davis, Chapel Hill; Loretta V. Willis; Robert E. Johnston, both of Raleigh, all of N.C.; Jonathan F. Smith, Frederick, Md.

[73] Assignee: North Carolina State University, Raleigh, N.C.

[21] Appl. No.: 369,023

[22] Filed: Jun. 20, 1989

[51] Int. Cl.$^5$ .................. C12N 15/40; C12N 7/01; C12N 7/04; A61K 39/193
[52] U.S. Cl. .............................. 536/237.2; 435/235.1; 435/236; 435/320.1; 424/89; 424/93 A; 935/10; 935/65
[58] Field of Search ............... 435/235.1, 236, 320.1, 435/172.3; 536/27; 424/89, 93; 935/32, 56, 57, 65, 10

[56] References Cited

PUBLICATIONS

Rice, C. M. et al. 1987, *J. Virol.* vol. 61 pp. 3809–3819.
Joklik, W. et al. 1980, *Zinsser Microbiology* 17th Edition, pp. 1014–1015.
Rice, C. M. et al. 1989, *The New Biologist* vol. 1 No. 3 pp. 285–296.
Roberts, J. D. et al. 1988, *Science* vol. 242 pp. 1171–1173.
Polo, J. et al. 1988, *Journal of Virology* vol. 62, No. 6, pp. 2124–2133.
Dente, L. et al. 1983 *Nucleic Acids Research* vol. 11, No. 6, pp. 1645–1655.
BRL Catalog, 1988, Bethesda Research Laboratories, Gathersburg, Md. p. 68.
Johnson, B. et al. 1986, *Journal of General Virology*, vol. 67, pp. 1951–1960.
N. Davis et al., *Virology* 183, 20–31 (1991).
R. Kinney et al., *Virology* 152, 400–413 (1986).
Johnston, R. and Smith, J., "Selection for Accelerated Penetration in Cell Culture Coselects for Attenuated Mutants of Venezuelan Equine Encephalitis Virus," *Virology* 162, 437 (1988).
Kinney, R. et al., "The Full-Length Nucleotide Sequences of the Virulent Trinidad Donkey Strain of Venezuelan Equine Encephalitis Virus and Its Attenuated Vaccine Derivative, Strain TC–83," *Virology* 170, 19 (1989).
Baric, R. et al., "A Sindbis Virus Variant with a Cell-Determined Latent Period," *Virology* 110, 237 (1981).
Baric, R. et al., "In Vitro Selection of an Attenuated Variant of Sindbis Virus", 685, Animal Virus Genetics, B. N. Fields and R. Jaenisch, Eds., (Academic Press, New York, 1980).
Olmsted, R. et al., "Sindbis Virus Mutants Selected for Rapid Growth in Cell Culture Display Attenuated Virulence in Animals," *Science* 225, 424 (1984).
Olmsted, R. et al., "Characterization of Sindbis Virus Epitopes Important for Penetration in Cell Culture and Pathogenesis in Animals," *Virology* 148, 245 (1986).
Davis, N. et al., "A Single Nucleotide Change in the E2 Glycoprotein Gene of Sindbis Virus Affects Penetration Rate in Cell Culture and Virulence in Neonatal Mice," *Proc. Natl. Acad. Sci. USA* 83, 6221 (1986).
Johnston, R. et al., "Nucleic Acid Sequence Analysis of Sindbis Pathogenesis And Penetration Mutants," *Positive Strand RNA Viruses*, 467 (1987).

*Primary Examiner*—Richard A. Schwartz
*Assistant Examiner*—Mary E. Mosher
*Attorney, Agent, or Firm*—Bell, Seltzer, Park & Gibson

[57] ABSTRACT

A DNA comprises a cDNA clone coding for an infectious Venezuelan Equine Encephalitis Virus RNA transcript and a heterologous promoter sequence positioned upstream from the cDNA clone and operatively associated therewith. A method of making a live attenuated Togavirus useful as a vaccine, and cDNA clones which code for attenuated Togaviruses, is also disclosed.

5 Claims, 11 Drawing Sheets

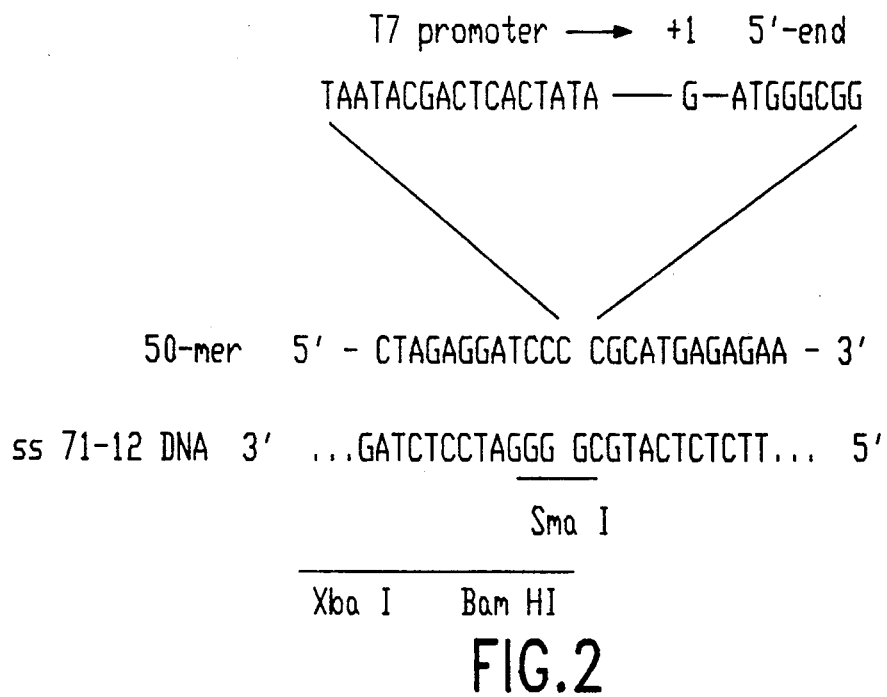

FIG.2

```
                   1      7
Genome RNA              m GpppAUGGGCGGCGYAYGAGAGAA(N)
                                                      18 ...
Direct
sequencing on           N...NUGGGCGGCGCA...
genome RNA  2

3
Clone 71-12                      GCATGAGAGAAGCCCAGACCAATTACCTACCCAAA
```

Met Glu Lys Val His Val Asp Ile Glu Glu Asp Ser
ATG GAG AAA GTT CAC GTT GAC ATC GAG GAA GAC AGC

Pro Phe Leu Arg Ala Leu Gln Arg Thr Phe Pro Gln
CCA TTC CTC AGA GCT TTG CAG CGG ACG TTC CCG CAG

Phe Glu Val Glu Ala Lys Gln Val Thr Asp Asn Asp
TTT GAG GTA GAA GCC AAG CAG GTC ACT GAT AAT GAC

His Ala Asn Asp Gln Ser Val ...
CAT GCT AAT GAC CAG AGC GTT

← VEE virion RNA

FIG. 5

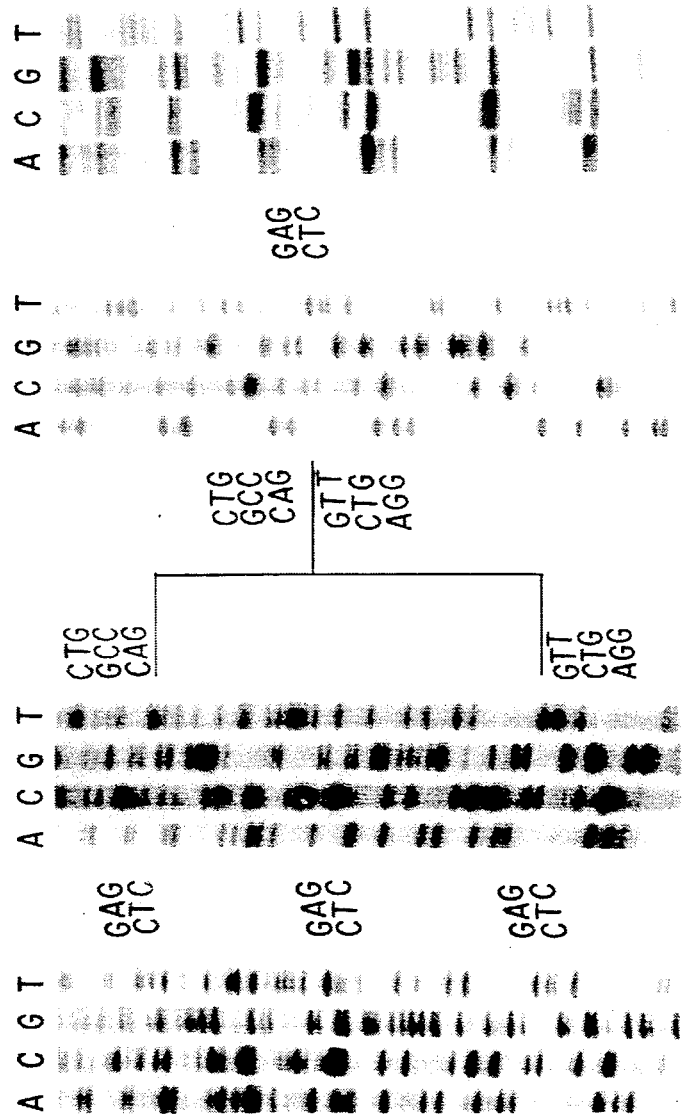

1
Pro Pro His Pro Ala Pro Arg Thr Arg Thr Pro Ser Leu Ala Pro Ser
CCU CCA CAU CCC GCU CCG CGC ACA AGA ACA CCG UCA CUU GCA CCC AGC
1

17
Arg Ala Cys Ser Arg Thr Ser Leu Val Ser Thr Pro Pro Gly Val Asn
AGG GCC UGC UCG AGA ACC AGC CUA GUU UCC ACC CCG CCA GGC GUG AAU
49

33
Arg Val Ile Thr Arg Glu Glu Leu Glu Ala Leu Thr Pro Ser Arg Thr
AGG GUG AUC ACU AGA GAG GAG CUC GAG GCG CUU ACC CCG UCA CGC ACU
97

49
Pro Ser Arg Ser Val Ser Arg Thr Ser Leu Val Ser Asn Pro Pro Gly
CCU AGC AGG UCG GUC UCG AGA ACC AGC CUG GUC UCC AAC CCG CCA GGC
145

65
Val Asn Arg Val Ile Thr Arg Glu Glu Phe Glu Ala Phe Val Ala Gln
GUA AAU AGG GUG AUU ACA AGA GAG GAG UUU GAG GCG UUC GUA GCA CAA
193

81
Gln Gln Op* Arg Phe Asp Ala Gly Ala Tyr Ile Phe Ser Ser Asp Thr
CAA CAA UGA CGG UUU GAU GCG GGU GCA UAC AUC UUU UCC UCC GAC ACC
241

97
Gly Gln Gly His Leu Gln Gln Lys Ser Val Arg Gln Thr Val Leu Ser
GGU CAA GGG CAU UUA CAA CAA AAA UCA GUA AGG CAA ACG GUG CUA UCC
289

FIG.8

```
113
Glu Val Val Leu Glu Arg Thr Glu Leu Glu Ile Ser Tyr Ala Pro Arg
GAA GUG GUG UUG GAG AGG ACC GAA UUG GAG AUU UCG UAU GCC CCG CGC
337

129
Leu Asp Gln Glu Lys Glu Glu Leu Leu Arg Lys Lys Leu Gln Leu Asn
CUC GAC CAA GAA AAA GAA GAA UUA CUA CGC AAG AAA UUA CAG UUA AAU
385

145
Pro Thr Pro Ala Asn Arg Ser Arg Tyr Gln Ser Arg Lys Val Glu Asn
CCC ACA CCU GCU AAC AGA AGC AGA UAC CAG UCC AGG AAG GUG GAG AAC
433

161
Met Lys Ala Ile Thr Ala Arg Arg Ile Leu Gln Gly Leu Gly His Tyr
AUG AAA GCC AUA ACA GCU AGA CGU AUU CUG CAA GGC CUA GGG CUA UAU
481
```

FIG. 8(CONT.)

$\Delta G = -95.0$ kcal

| | % Penetration-15 min. | % Mortality in mice |
|---|---|---|
| VEE-TRD —— Glu —— Thr —— Glu —— Lys —— COOH<br>NH₂   76  120  209  245  423<br>         GAG  ACA  GAG  AAA | 12 | 100 |
| FC-4-2 —— Lys —— Lys //<br>         AAG   AAA | 76 | 0 |
| FC-4-7 —— Lys //<br>         AAA | 92 | 0 |
| FC-1-2 —— Lys //<br>         AAG | 66 | 0 |
| FC-4-1 —— Lys //<br>         AAG | 73 | 0 |
| FC-4-6 —— Lys —— Asn //<br>         AAG   AAU | 53 | 0 |

E2 Glycoprotein

FIG. 10

CDNA CLONE CODING FOR VENEZUELAN EQUINE ENCEPHALITIS VIRUS AND ATTENUATING MUTATIONS THEREOF

The U.S. Government has a nonexclusive, nontransferable, irrevocable paid-up license to practice or have practiced this invention for or on its behalf as provided by the terms of Contract No. DAMD 17-87-C-7259 awarded by the U.S. Department of the Army and Contract No. NS26681 awarded by the National Institutes of Health.

BACKGROUND OF THE INVENTION

Venezuelan equine encephalitis virus (VEE) is a member of the alphavirus genus of the Togaviridae. The viral genome is a single-stranded, messenger-sense RNA, modified at the 5'-end with a methylated cap, and at the 3'-end with a variable-length poly (A) tract. Structural subunits containing a single viral protein, C, associate with the RNA genome in an icosahedral nucleocapsid. In the virion, the capsid is surrounded by a lipid envelope covered with a regular array of transmembranal protein spikes, each of which consists of a heterodimeric complex of two glycoproteins, E1 and E2 (Pedersen and Eddy, 1974). Although incompletely studied, the organization of the VEE genome and the overall strategy of VEE gene expression presumably parallel those of the prototype alphaviruses, Sindbis virus and Semliki Forest virus (reviewed in Schlesinger and Schlesinger, 1986). For example, details of the partial genome sequence (Kinney et al., 1986) demonstrate that VEE structural proteins are translated in the form of a polyprotein from a 26S subgenomic mRNA which corresponds to the 3'-one third of the viral genome. Proteolytic processing produces the proteins found in the mature virion. Alphavirus nonstructural protein genes are located in the 5'-two thirds of the genome in the order nsP1, nsP2, nsP3 and nsP4. The proteins are expressed initially as polyprotein pre cursors and then proteolytically processed to their mature forms (Keranen and Ruohonen, 1983; Strauss et al., 1984; Hardy and Strauss, 1988). The mature nonstructural proteins are required or replication of genome RNA and the synthesis of 26S subgenomic mRNA.

VEE, which was first isolated during a serious epizootic in Venezuela in the mid 1930's (Kubes and Rios, 1939), continues to be a significant public health problem in South and Central America. The natural enzootic cycle has been described in many areas, reaching as far north as Florida. In these foci, the virus can be isolated from mosquitoes as well as equines and other vertebrate species. The equine disease induced by enzootic strains is relatively benign (Henderson et al., 1971; Scherer and Chin, 1977). In contrast, combined data from the study of VEE epizootics show involvement of different mosquito species and antigenically distinct strains of VEE (Young and Johnson, 1969; Scherer and Chin, 1977; Trent et al., 1979). Epizootic strains of VEE cause much more severe equine disease with fatality rates as high as 83% (Groot, 1972). Acute febrile disease in humans is associated with VEE epidemics, is often very widespread, but is usually relatively mild. Severe neurologic disease, including fatal encephalitis, is most frequent in children, with case-fatality rates as high as 0.7% (Groot, 1972).

Preventive measures include yearly vaccination of horses with an inactivated VEE vaccine and control of mosquito populations. An experimental live vaccine, TC-83 (Berge et al., 1961) was used to protect large numbers of horses during the 1971 Texas outbreak, and is routinely used to immunize laboratory workers. The serious side effects and less than 100% effectiveness associated with this vaccine limit its usefulness for humans. The unpredictable nature of VEE epidemics, the demonstrated capability of VEE to spread over large areas, the increased virulence of epidemic strains, and the inadequacies of the TC-83 vaccine indicate a need for further understanding of VEE epidemiology, biology and pathogenesis.

Full-length cDNA clones of positive-strand RNA viruses are important tools for the study of the biology of this group of viruses. It has been demonstrated in numerous virus systems that in vitro transcripts of cDNA clones, and in some cases the cDNA itself, can initiate a complete and productive infectious cycle upon introduction into susceptible cells (for examples, see Racaniello and Baltimore, 1981; Ahlquist et al., 1984; Kaplan et al., 1985; Mizutani and Colonno, 1985; van der Werf, 1986; Rice et al., 1987; Vos et al., 1988). This has made it possible to test progeny virus for phenotypic manifestations of directed mutations and recombinations which have been introduced into the cDNA clone. Pathogenesis studies with several positive-strand viruses, including the picornaviruses (La Monica et al., 1986; La Monica et al., 1987; Nomoto et al., 1987) and the alphaviruses (Polo et al., 1988; Lustig et al., 1988) have been advanced significantly by the use of full-length cDNA clones.

We herein describe the construction of a cDNA clone of the VEE genome downstream from a synthetic T7 promoter. In vitro transcription of this clone with the T7 RNA polymerase yielded infectious VEE RNA. In addition, analysis of this cDNA clone led to the discovery of a large sequence duplication near the 3'-end of the VEE nsP3 gene.

CITED REFERENCES

The following references are cited herein.

Ahlquist, P., French, R., Janda, M., and Loesch-Fries, S. (1984). Multicomponent RNA plant virus infection derived from cloned viral cDNA. Proc. Natl. Acad. Sci. USA 81, 7066–7070.

Ausubel, F. M., Brent, R., Kingston, R. E., Moore, D. D., Seidman, J. G., Smith, J. A., and Struhl, K. (Eds.) (1987). "Current Protocols in Molecular Biology." John Wiley & Sons, New York.

Berge, T. O., Banks, I. S., and Tigertt, W. D. (1961). Attenuation of Venezuelan equine encephalomyelitis virus by in vitro cultivation in guinea pig heart cells. Am. J. Hyg. 73, 209–218.

Brandt, W. E., Buescher, E. L., and Hetrick, F. M. (1969). Production and characterization of arbovirus antibody in mouse ascitic fluid. Am. J. Trop. Med. Hyg. 16, 339–347.

Chen, E. Y., and Seeburg, P. H. (1985). Supercoil sequencing: a fast and simple method for sequencing plasmid DNA. DNA Lab. Methods 4, 165–170.

Davis, N. L., Fuller, F. J., Dougherty, W. G., Olmsted, R. A. and Johnston, R. E. (1986). A single nucleotide change in the E2 glycoprotein gene of Sindbis virus affects penetration rate in cell culture and virulence in neonatal mice. Proc. Nat'l. Acad. Sci. USA 83, 6771–6775.

Faragher, S. G., Meek, A. D. J., Rice, C. M., and Dalgarno, L. (1988). Genome sequences of a mouseavirulent and a mouse-virulent strain of Ross River virus. Virology 163, 509–526.

Groot, H. (1972). The health and economic impact of Venezuelan equine encephalitis (VEE). In "Venezuelan Encephalitis." Pan American Health Organization, Washington, D.C. pp. 7–16.

Gubler, U., and Hoffman, B. J. (1983). A simple and very efficient method for generating cDNA libraries. Gene 25, 263–269.

Hardy, W. R., and Strauss, J. H. (1988). Processing the non structural polyproteins of Sindbis virus: study of the kinetics in vivo by using monospecific antibodies. J. Virol. 62, 998–1007.

Hanahan, D., and Meselson, M. (1980). Plasmid screening at high colony density. Gene 10, 63–67.

Henderson, B. E., Chapell, W. A., Johnston, J. G., and Sudia, W. D. (1971). Experimental infection of horses with three strains of Venezuelan equine encephalomyelitis virus. Am. J. Epidem. 93, 194–205.

Hollifield, W. C., Kaplan, E. N., and Huang, H. V. (1987). Efficient RecABC-dependent, homologous recombination between coliphage lambda and plasmids requires a phage ninR region gene. Mol. Gen. Genetics 210, 248–255.

Holmes, D. S., and Quigley, M. (1981). A rapid boiling method for the preparation of bacterial plasmids. Anal. Biochem. 114, 193–197.

Johnston, R. E., MacKenzie, J. M., and Dougherty, W. G. (1986). Assembly of overlapping DNA sequences by a program written in BASIC for 64K CP/M and MS-DOS IBM-compatible microcomputers. Nucleic Acids Res. 14, 17–527.

Johnston, R. E., and Smith, J. F. (1988). Selection for accelerated penetration in cell culture co-selects for attenuated mutants of Venezuelan equine encephalitis virus. Virology 162, 437–443.

Kaplan, G., Lubinski, J., Dasgupta, A., and Racaniello, V. R. (1985). In vitro synthesis of infectious poliovirus RNA. Proc. Natl. Acad. Sci. USA 82, 8424–8428.

Keranen, S., and Ruohonen, L. (1983). Nonstructural proteins of Semliki Forest virus: synthesis, processing, and stability in infected cells. J. Virol. 47, 505–551.

Kinney, R. M., Johnson, B. J. B., Brown, V. L., and Trent, D. W. (1986). Nucleotide sequence of the 26S mRNA of the virulent Trinidad donkey strain of VEE virus and deduced sequence of the encoded structural protein. Virology 152, 400–413.

Kozak, M. (1981). Possible role of flanking nucleotides in recognition of the AUG initiator codon by eukaryotic ribosomes. Nucleic Acids Res. 9, 5233–5252.

Kubes, V., and Rios, F. A. (1939). The causitive agent of infectious equine encephalomyelitis in Venezuela. Science 90, 20–21.

Kunkel, T. A. (1985). Rapid and efficient site-specific mutagenesis without phenotypic selection. Proc. Nat'l. Acad. Sci. (USA) 82, 488–492.

La Monica, N., Meriam, C., and Racaniello, V. R. (1986). Mapping of sequences required for mouse neurovirulence of poliovirus type 2 Lansing. J. Virol. 57, 515–525.

LaMonica, N., Almond, J. W., and RaCaniello, V. R. (1987). A mouse model for poliovirus neurovirulence identifies mutations that attenuate the virus for humans. J. Virol. 61, 2917–2920.

Levis, R., Weiss, B. G., Tsiang, M., Huang, H., and Schlesinger, S. (1986). Deletion mapping of Sindbis virus DI RNAs derived from cDNAs defines the sequences essential for replication and packaging. Cell 44, 137–145.

Lustig, S., Jackson, A. C., Hahn, C. S., Griffin, D. E., Strauss, E. G., and Strauss, J. H. Molecular basis of Sindbis virus neurovirulence in mice. J. of Virol. 62, 2329–2336.

Maniatis, T., Fritsch, E. F., and Sambrook, J. (1982). "Molecular Cloning: A Laboratory Manual." Cold Spring Harbor Laboratory, Cold Spring Harbor, N.Y.

Milligan, J. F., Groebe, D. R., Witherell, G. W., and Uhlenbeck, 0. C. (1987). Oligoribonucleotide synthesis using T7 RNA polymerase and synthetic DNA templates. Nucleic Acids Res. 15, 8783–8798.

Mizutani, S., and Colonno, R. J. (1985). In vitro synthesis of an infectious RNA from cDNA clones of human rhinovirus type 14. J. Virol. 56, 628–632.

Nielsen, D. A., and Shapiro, D. J. (1986). Preparation of capped RNA transcripts using T7 RNA polymerase. Nucleic Acids Res. 14, 5936.

Nomoto, A., Kohara, M., Kuge, S., Kawamura, N., Arita, M., Komatsu, T., Abe, S., Semler, B. L., Wimmer, E., and Itoh, H. (1987). Study on virulence of poliovirus type 1 using in vitro modified viruses. In "Positive Strand RNA Viruses" (M. A. Brinton and R. R. Rueckert, Eds.), pp. 437–452. Alan R. Liss, Inc. New York.

Ou. J-H., Strauss, E. G., and Strauss, J. H. (1983). The 5'- terminal sequences of the genomic RNAs of several alphaviruses. J. Mol. Biol. 168, 1–15.

Pedersen, C. E., and Eddy, G. A. (1974). Separation, isolation and immunological studies of the structural proteins of Venezuelan equine encephalitis virus. J. Virol. 14, 40–744.

Peranen, J., Takkinen, K., Kalkkinen, N., and Kaariainen, L. (1988). Semliki Forest virus-specific nonstructural protein nsP3 is a phosphoprotein. J. Gen. Virol. 69, 2165–2178.

Polo, J. M., Davis, N. L., Rice, C. M., Huang, H. V., and Johnston R. E. (1988). Molecular analysis of Sindbis virus pathogenesis in neonatal mice by using virus recombinants constructed in vitro. J. Virol. 62, 2124–2133.

Porterfield, J. S. (1980). Antigenic characteristics and classification of Togaviridae. In "The Togaviruses" (R. W. Schlesinger, Ed.), pp. 13–46. Academic Press, Inc., New York.

Racaniello, V. R., and Baltimore, D. (1981). Cloned poliovirus complementary DNA is infectious in mammalian cells. Science 214, 916–919.

Rice, C. M., Levis, R., Strauss, J. H., and Huang, H. V. (1987). Production of infectious transcripts from Sindbis virus cDNA clones: mapping of lethal mutations, rescue of a temperature-sensitive marker and in vitro mutagenesis to generate defined mutants. J. Virol. 61, 809–3819.

Rosa, M. D. (1980). DNA sequence for the T7 RNA polymerase promoter for T7 RNA species II. J. Mol. Biol. 47, 199–204.

Scherer, W. F., and Chin, J. (1977). Responses of guinea pigs to infections with strains of Venezuelan equine encephalitis virus and correlations with equine virulence. Am. J. Trop. Med. and Hygiene 26, 307–312.

Schlesinger, S., and Schlesinger, M. J. (Eds.) (1986). The Togaviridae and Flaviviridae. Plenum Publishing Corp., New York.

Strauss, E. G., Rice, C. M., and Strauss, J. H. (1984). Complete nucleotide sequence of the genomic RNA of Sindbis virus. Virology 133, 92–110.

Strauss, E. G., and Strauss, J. H. (1986). Structure and replication of the alphavirus genome. In "The Togaviridae and Flaviviridae" (S. Schlesinger and M. J. Schlesinger, Eds.), pp. 35-90. Plenum Press, New York.

Strauss, J. H., Strauss, E. G., Hahn, C. S., Hahn, Y. S., Galler, R., Hardy, W. R., and Rice, C. M. (1987). Replication of alphaviruses and flaviviruses: proteolytic processing of polyproteins. In "Positive Strand RNA Viruses" (M. A. Brinton and R. R. Rueckert, Eds.), pp. 209-225. Alan R. Liss, Inc. New York.

Sreevalsan, T., Lockart, Jr., R. Z., Dodson, Jr., M. L., and Hartman, K. A. (1968). Replication of western equine encephalomyelitis virus I. Some chemical and physical characteristics of viral ribonucleic acid. J. Virol. 2, 558-566.

Takkinin, O. (1986). Complete nucleotide sequence of the nonstructural protein genes of Semliki Forest virus. Nucleic Acids Res. 14, 5667-5682.

Trent, D. W., Clewly, J. P., France, J. K., and Bishop, D. H. L. (1980). Molecular aspects of antigenic and biological variation: the Venezuelan equine encephalitis viruses. In "International Symposium on Tropical Arboviruses and Haemorrhagic Fevers" (F. de Paula Pinheiro, Ed.), pp. 83-103. Brazilian Academy of Sciences. van der Werf, S., Bradley, J., Wimmer, E., Studier, F. W., and Dunn, J. J. (1986). Synthesis of infectious poliovirus RNA by purified T7 RNA polymerase. Proc. Nat'l. Acad. Sci. (USA) 83, 2330-2334.

Vieira, J., and Messing, J. (1987). Production of single-stranded plasmid DNA. Methods in Enzymology. In press.

Vos, p , Jaegle, M., Wellink, J., Verver, J., Eggen, R., Van Kammen, A., and Goldbach, R. Infectious RNA transcripts derived from full-length DNA copies of the genomic RNAs of cowpea mosaic virus. Virology 165, 33-41.

Young, N. A., and Johnson, K. M. (1969). Antigenic variants of Venezuelan equine encephalitis virus: their geographic distribution and epidemiologic significance. Am. J. Epidemiology 89, 286-307.

Zuker, M., and Stiegler, P. (1981). Optimal computer folding of large RNA sequences using thermodynamics and auxiliary information. Nuc. Acids Res. 9, 133-148.

SUMMARY OF THE INVENTION

A first aspect of the present invention is a single-stranded DNA sequence comprising a cDNA clone coding for an infectious Venezuelan Equine Encephalitis (VEE) Virus RNA transcript and a heterologous promoter sequence positioned upstream from said cDNA clone and operatively associated therewith. Preferably at least one attenuating mutation is included in the cDNA clone, and more preferably at least two attenuating mutations are included in the cDNA clone. Attenuating mutations may, for example, be provided in the E2 coding region of the cDNA clone.

A novel method of making DNA sequences such as the foregoing is also disclosed herein. Thus, a second aspect of the present invention is a method of making a live attenuated Togavirus useful as a vaccine. This method comprises the steps of (a) generating a cDNA clone coding for an RNA sequence capable of producing an infectious and virulent Togavirus; (b) independently identifying at least one attenuating mutation capable of reducing the virulence of the Togavirus; (c) modifying the cDNA clone to incorporate the at least one attenuating mutation therein; (d) joining the cDNA clone to a heterologous promoter sequence, wherein the heterologous promoter sequence is positioned upstream of the cDNA clone and operatively associated therewith, to thereby form a DNA sequence; (e) synthesizing an RNA sequence from the DNA sequence; and then (f) transfecting a Togavirus-permissive cell with the RNA sequence; whereby live attenuated Togavirus particles are produced by the transfected cell.

A third aspect of the present invention is a single-stranded DNA sequence comprising a cDNA clone coding for an infectious Togavirus, the cDNA clone including at least one attenuating mutation therein, the DNA sequence further comprising a heterologous promoter sequence positioned upstream from the cDNA clone and operatively associated therewith.

The foregoing and other aspects of the present invention are explained in the drawings, detailed description, and examples which follow.

BRIEF DESCRIPTION OF THE DRAWINGS

FIG. 2. Annealing of the 50-nucleotide mutagenesis primer to single-stranded DNA from cDNA clone 71-12. Single-stranded (ss) 71-12 DNA was isolated from E. coli CJ236 (dut$^-$ung$^-$) transformants as described in the Examples. The junction between the multiple cloning region and the upstream terminus of the cDNA insert is shown. The synthetic 50-nucleotide primer (50-mer) was annealed to 71-12 ssDNA by 12-nucleotides at both its 5'- and 3'- ends and the hybrid was used in the in vitro mutagenesis protocol of Kunkel (1985). T7 promoter, the untranscribed portion of the consensus T7 promoter (Rosa, 1980); +1, the first nucleotide transcribed; 5'-end, the 5'-most 8 nucleotides of the VEE genome; Sma I, Xba I, Bam HI, restriction sites in the multiple cloning region of pUC118.

FIG. 3. Sequence of the 5'-end of the VEE genome. Nucleotide sequences obtained for overlapping portions of the 5'-end of the VEE genome. 1, published sequence of the 5'-end of VEE (Trinidad donkey strain) genomic RNA (Ou et al., 1983); 2, sequence obtained by dideoxynucleotide chain-termination method with the V12 primer on VEE virion RNA; 3, sequence of the upstream terminus of cDNA clone 71-12, obtained by dideoxynucleotide chain-termination method on both rescued single-stranded and heat-denatured double-stranded 71-12 DNA.

FIG. 5. Agarose gel electrophoresis of transcription reactions with and without nuclease treatment. Transcription reaction mixes were denatured, electrophoresed through 0.8% agarose gel and stained with ethidium bromide. Lane 1: Untranscribed Not I-digested pV1000 DNA. Lane 2: Reaction treated with DNase I before addition of T7 RNA polymerase. Lane 3: Reaction treated with DNase I after transcription. Lane 4: Reaction treated with RNase A after transcription. Lane 5: Untreated transcription reaction. Lane 6: Reaction incubated at 4C.

FIG. 7A-D Comparison of sequences obtained from VEE virion RNA, cDNA clone 3-31, pV1002 DNA and RNA from virions produced by transfection with pV1002 transcripts. Sequence data were obtained using the V13 oligonucleotide primer in the dideoxynucleotide chain-termination method with (A) VEE virion RNA, (B) single-stranded DNA rescued from clone 3-31, (C) single-stranded M13 DNA containing the subcloned 3.3 kbp Hind III fragment of pV1002, and (D) RNA purified from pV1002 progeny virions. CTCGAG is the recognition site for Xho I.

FIG. 8. The VEE genomic sequence in the region of the pV1000 deletion with the predicted amino acid sequence. Nucleotides are numbered from 1 to 528. The sequence between nucleotides 1 and 396 was obtained from both strands of primary cDNA clones using the V13 and V14 sequencing primers, and from VEE virion RNA using the V13 primer. Overlapping portions of the sequence between nucleotides 273 and 528 were obtained from five different primary cDNA clones using three different sequencing primers. The two tandem repeats are underlined and separated by a diagonal; the sequence deleted in pV1002 is marked with a bold line; the opal codon and the consensus cleavage site are boxed.

FIG. 10 illustrated attenuating mutations in the E2 glycoprotein coding region of VEE useful for practicing the present invention.

DETAILED DESCRIPTION OF THE INVENTION

Figure 1:
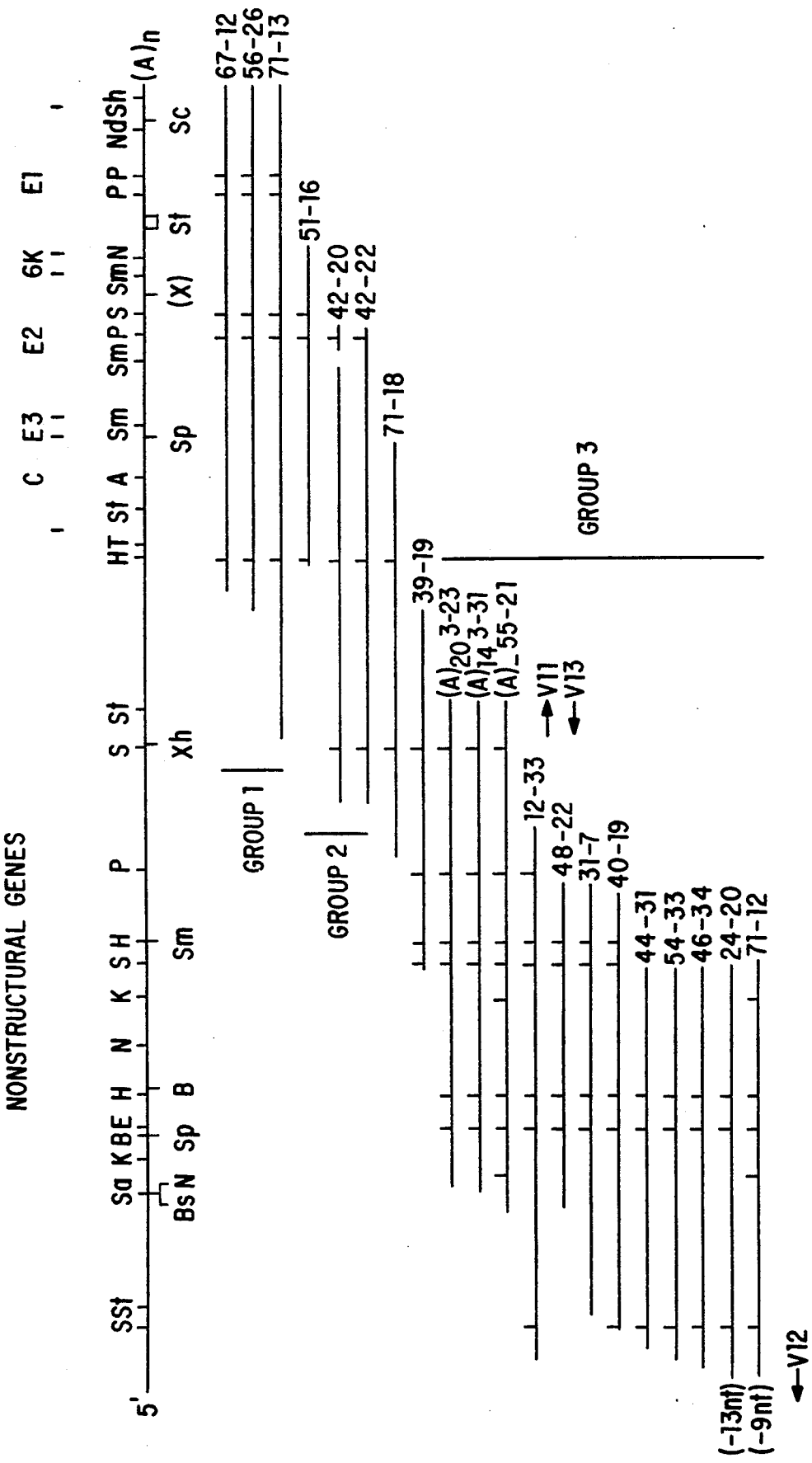
FIG. 1. VEE cDNA clone library and partial restriction map. The alignment of selected cDNA clones was based on results of restriction enzyme digests and sequence analysis. Sites for 19 enzymes are shown. Map distances in the nonstructural gene region were estimated from relative migration rates of restriction fragments in agarose gels. Vertical bars show some of the restriction sites mapped on the cDNAs. Structural genes are designated C (capsid), E3, E2, 6K and El. V11, V12, and V13 are oligonucleotide sequencing primers. The following abbreviations are used: (A)n, poly (A) tract; A, Afl II; B, Bam HI; Bs, Bss HII; E, Eco RI; H, Hind III; K, Kpn I; N, Nae I; Nd, Nde I; P, Pst I; S, Sac I; Sa, Sal I; Sc, Sac II; Sh, Sph I; Sm, Sma I; Sp, Spe I; St, Stu I; T, Tth 111 I; X, Xba I; Xh, Xho I.

The Togavirus cDNA clones employed in practicing the present invention are genomic clones which code for an RNA transcript, which RNA transcript is capable of producing live encapsidated Togavirus when used to transfect a Togavirus-permissive cell.

Exemplary Togaviruses useful in practicing the present invention include, but are not limited to, Eastern Equine Encephalitis virus, Venezuelan Equine Encephalitis virus, Western Equine Encephalitis virus, Sindbis virus, Chikungunya virus, Semliki Forest virus, Mayaro virus, Marituba virus, Ross River virus, and Rubella virus. Preferred are those Togaviruses in the genus Alphavirus, with Venezuelan Equine Encephalitis virus most preferred.

Togavirus-permissive cells, alphavirus-permissive cells, and VEE-permissive cells are cells which, upon transfection with the viral RNA transcript, are capable of producing viral particles. Togaviruses have a broad host range. Examples of such cells include, but are not limited to, Vero cells, baby hamster kidney cells, and chicken embryo fibroblast cells. Uptake of the RNA into the cells can be achieved by any suitable means, such as, for example, by treating the cells with DEAE-dextran, treating the cells with "LIPOFECTIN", and by electroporesis.

The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art. See, e.o.. B. Davis, R. Dulbecco, H. Eisen, and H. Ginsberg, *Microbiology*, 132 (3d ed. 1980), whether the mutation be a substitution mutation or an in-frame deletion mutation. The phrase "attenuating mutation" excludes mutations which would be lethal to the virus.

Promoter sequences and Togavirus cDNA clones are operatively associated in the present invention such that the promoter causes the cDNA clone to be transcribed in the presence of an RNA polymerase which binds to the promoter. The promoter is positioned on the 5'end (with respect to the virion RNA sequence), or "upstream" from, the cDNA clone. An excessive number of nucleotides between the promoter sequence and the cDNA clone will result in the inoperability of the construct. Hence, the number of nucleotides between the promoter sequence and the cDNA clone is preferably not more than eight, more preferably not more than 5, still more preferably not more than 3, and most preferably not more than 1. Exemplary promoters useful in the present invention include, but are not limited to, T3 promoters, T7 promoters, and SP6 promoters. The DNA sequence of the present invention may reside in any suitable transcription vector. The DNA sequence preferably has a complementary DNA sequence bonded thereto so that the double-stranded sequence will serve as an active template for RNA polymerase. Hence, the transcription vector preferably comprises a plasmid. When the DNA sequence comprises a plasmid, it is preferred that a unique restriction site be provided 3'(with respect to the virion RNA sequence) to ("downstream" from) the cDNA clone. This provides a means for linearizing the DNA sequence to enhance the efficiency of transcription of genome-length RNA in vitro.

The cDNA clone can be generated by any of a variety of standard methods. A preferred method is the method of Gubler and Hoffman (1983). Attenuating mutations of Togaviruses are identified by sequencing attenuated strains of the Togavirus of interest and comparing the sequence of the attenuated strain with the sequence of the corresponding wild-type virus. Serial passage techniques for the generation of attenuated strains may be carried out in accordance with known procedures. Preferably, the attenuated strains are generated by selecting strains at each passage during serial passage in cell culture which either grow rapidly or penetrate the cell more rapidly. This selection process, which reduces the number of serial passages required to obtain attenuated strains, is known. See, e.g., Olmstead et al., 225 Science 424 (1984); Johnston and Smith, 162 Virology 437 (1988). cDNA clones may be modified to incorporate attenuating mutations by site-directed mutagenesis in accordance with known procedures. An exemplary technique is that of Kunkel (1985). These same techniques may be used to join the heterologous promoter to the cDNA clone.

RNA is preferably synthesized from the DNA sequence in vitro using purified RNA polymerase in the presence of ribonucleotide triphosphates in accordance with known procedures.

Vaccines of the present invention comprise an immunogenic amount of a live attenuated virus as disclosed herein in combination with a pharmaceutically acceptable carrier. An "immunogenic amount" is an amount of the attenuated virus sufficient to evoke an immune response in the subject to which the vaccine is administered. An amount of from about $10^1$ to about $10^5$ plaque forming units per dose is believed suitable, depending upon the age and species of the subject being treated. Exemplary pharmaceutically acceptable carriers include, but are not limited to, sterile pyrogen-free water and sterile pyrogen-free physiological saline solution. Subjects which may be administered immunogenic amounts of the live attenuated viruses of the present invention include both human and animal (e.g., horse, donkey, mouse, hamster, monkeys) subjects. Administration may be by any suitable means, such as intraperitoneal or intramuscular injection.

Complementary DNA clones of the Venezuelan Equine Encephalitis virus are made in accordance with the procedures described herein, as supplemented with procedures known in the art. We employed as a starting material the Trinidad donkey strain of VEE virus (See Example 1 below). Additional guidance is provided by the RNA sequence of the Trinidad donkey Strain of VEE set forth in R. Kinney et al., *The Full-Length Nucleotide Sequences of the Virulent Trinidad Donkey Strain of Venezuelan Equine Encephalitis Virus and Its Attenuated Vaccine Derivative, Strain TC-83*, 70 Virology 19 (1989).

A first exemplary attenuating substitution mutation in a VEE cDNA clone useful in practicing the present invention is a substitution mutation which codes for an attenuating amino acid, preferably an amino acid selected from the group consisting of lysine, arginine, and histidine, as E2 amino acid 76.

A second exemplary attenuating substitution mutation in a VEE cDNA clone useful in practicing the present invention is a substitution mutation which codes for an attenuating amino acid, preferably an amino acid selected from the group consisting of lysine, arginine, and histidine, as E2 amino acid 120.

A third exemplary attenuating substitution mutation in a VEE cDNA clone useful in practicing the present invention is a substitution mutation which codes for an attenuating amino acid, preferably an amino acid selected from the group consisting of lysine, arginine, and histidine, as E2 amino acid 209.

The present invention is explained in greater detail in the examples which follow. These examples are provided for illustrative purposes only, and are not to be taken as limiting of the invention.

EXAMPLE 1

Cells, Virus and Virion RNA

BHK-21 cells (ATCC, passage 53) were maintained in Eagle's minimal essential medium (MEM), containing 10% tryptose phosphate broth, 5% fetal calf serum and 25 ug/ml gentamycin sulfate, and were used between passages 55 and 65. Secondary monolayer cultures of chick embryo fibroblasts (CEF) were grown in the same medium. Trinidad donkey strain of VEE virus was obtained from P. Jahrling, U.S. Army Medical Research Institute of Infectious Diseases, Ft. Detrick, Frederick, MD. This VEE isolate had been passed once in guinea pig brain and 14 times in embryonated eggs. Virus particles isolated by two cycles of equilibrium sedimentation were the source of genomic RNA, which was obtained by dissociation of virions with sodium dodecyl sulfate (SDS) and extraction with phenol-chloroform as described previously (Davis et al., 1986). This VEE virion RNA was the substrate for cDNA cloning, preparation of $^{32}$p-labeled, random-primed hybridization probes and direct sequencing by the dideoxy method (see below).

EXAMPLE 2

Recombinant DNA Procedures

Enzymatic manipulation, propagation and analysis of plasmid DNA were done essentially as described in Maniatis et al. (1982) and Ausubel et al. (1987). DNA was prepared by a modification of the boiling method of Holmes and Quigley (1981). Following removal of chromosomal DNA, the cell lysate was made 2M in ammonium acetate and incubated on ice for 1-2 hrs. This procedure precipitated most of the cellular RNA, which was removed by centrifugation before ethanol precipitation of plasmid DNA. DNA fragments were purified from agarose gels by electrophoresis onto DE-81 paper (Whatman Inc.) as described previously (Polo et al., 1988). Restriction enzymes and DNA modifying enzymes were purchased from Promega Corp., Bethesda Research Laboratories, Boehringer Mannheim, Amersham, or New England Biolabs, and used according to the supplier's instructions. cDNA clones containing more than two-thirds of the VEE genomic sequence were constructed and analyzed in an appropriate P3 facility at Fort Detrick, Md.

EXAMPLE 3

VEE cDNA Clones

Previously described techniques were used with slight modifications (Polo et al., 1988). Double-stranded cDNAs were generated by the technique of Gubler and Hoffman (1983) using avian myeloblastosis virus reverse transcriptase-XL (Life Sciences, Inc.) and an oligo d(T)$_{12-18}$ primer on VEE virion RNA. Klenow fragment of *E. coli* DNA polymerase I was used to convert uneven termini into blunt ends. The cDNAs were fractionated according to size by chromatography through Sephacryl S-1000 (Sigma) and the longest molecules were joined to pUCI18 DNA (Vieira and Messing, 1988) which had been linearized at its unique Sma I site. Ligation mixtures were used in transformation of competent *E. coli* HB101 cells (Bethesda Research Laboratories). Two-phase hybridizations with DNA from lysed bacterial colonies (colony lifts) were done on Biotrans nylon membranes (ICN) using standard procedures (Hanahan & Meselson, 1980). Colony lifts were screened with $^{32}$P-labeled first strand cDNA made from VEE virion RNA templates primed with a pd(N)$_6$ random primer (Pharmacia). Clones of ampicillin-resistant transformants which were found to carry the longest viral sequence inserts were used in further studies.

Clones were ordered with respect to one another and to the known sequence of the 3'-third of the genome (Kinney et al., 1986) by mapping of restriction enzyme sites and by sequence comparisons. The sequence of the 26S region predicts Pst I fragments of 0.8 and 1.2 kbp at the 3'-end of the genome. A subset of clones sharing this pattern were tentatively identified as 3'-end clones. Such clones, designated group 1, represented only slightly more than half of the total number with inserts over 3 kb, in spite of the fact that oligo d(T) was the primer for first strand cDNA synthesis. This was similar to our previous experience with Sindbis virus cDNAs (Polo et al., 1988). Sequence data from clone termini (see below) unequivocally identified several of the clones in group 1 as 3'-end clones and revealed the length of the poly (A) tract retained in each. Analysis of upstream (5'with respect to virion RNA) termini showed that some of these 3'-end clones extended beyond the 26S RNA transcription start site.

The longest clones in group 1 gave a Pst I- Hind III fragment of approximately 1.9 kb; a fragment of the same size also was found in a second group of clones (group 2) having only one Pst 1 site. Therefore, the clones of group 2 were predicted to extend from the 26S region into the nonstructural gene sequence, and to overlap cloned sequences in group 1. As expected, sequence information obtained from one end of clone 42-20, in group 2, correlated with a sequence within the E2 gene; sequence at the other terminus was not contained in the 26S region. The clones in group 3'which produced neither the Pst I fragments indicative of the 3,-end nor a 1.9 kbp Pst 1- Hind III fragment, shared a 0.3 kbp Hind III- Eco RI fragment which was not found in either of the other two groups. This final group was predicted to contain only nonstructural gene sequences, some of which might overlap with those in group 2. No terminal sequences obtained from clones in group 3 were found in the published 26S RNA sequence.

The grouping of 20 of the longest cDNA clones, shown in FIG. 1, was supported by more detailed restriction enzyme mapping and by two phase hybridization of plasmid DNA with the $^{32}$P-end- labeled, purified 0.3 kbp Hind III- Eco RI restriction fragment. However, the proposed overlap between groups 2 and 3 could not be proved by either of these techniques. As an alternative approach, a terminal sequence shared by three of the group 3 clones (3-23, 3-31, and 55-21) was used in the design of an oligonucleotide sequencing primer, V11 (labeled arrow in FIG. 1). The identity of the sequences obtained with this primer on cDNAs from group 2 (42-20, 42-22), clone 39-19, and group 3 (3-23, 3-31, 55-21) confirmed the overlap of these clones (FIG. 1).

EXAMPLE 4

DNA and RNA Sequence Analysis

The dideoxynucleotide chain termination method was used to obtain sequence data from both DNA and RNA templates. Termini of cDNA inserts were analyzed by a modification of the direct plasmid sequencing technique of Chen and Seeburg (1985) in which linearized, heat-denatured plasmid DNA was annealed to either the M13 universal sequencing primer or reverse sequencing primer. Other primers designed to anneal to specific VEE sequences were also used in this protocol (see below). Sequence information was obtained directly from RNA as described previously (Davis, et al., 1986). Single-stranded DNA templates were produced by superinfection of pUC118-JM101 transformants with a defective helper phage, M13K07 (Vieira and Messing, 1988), and purification of progeny phage DNA by standard methods (Ausubel et al., 1987). Single-stranded DNA sequencing reactions were constituted as described in Ausubel et al. (1987). Four VEE sequence-specific oligonucleotide primers were synthesized with an Applied Biosystems model 380A DNA synthesizer in either virion RNA sense [VII, d(AT-CAGTAAGGCAAACG), and V14, d(CCTCGAACAGTATT)], or complementary sense [V12, d(GTAGGTAATTGGTCTG), and V13, d(CGTTTGCCTTACTGATT)]. Sequences were analyzed using the Seqa lign (Johnston et al., 1986), Basmat matrix (R. E. Johnston, unpublished) and PC GENE programs.

EXAMPLE 5

Construction of pTX Cloning Vector

Totol101 vector sequences were separated from the SP6 promoter and Sindbis viral sequences by digestion at unique sites with Sac I and Xho I (Rice et al., 1987). Using standard techniques, the Pvu II fragment of pUC118 (Vieira and Messing, 1988) containing the multiple cloning region (322 bp) was joined to the Toto1101 vector fragment, and the resulting plasmid was cloned in E. coli HB101. A cloned plasmid of the correct size, pTX, had unique Hind III and Eco RI sites separated by an estimated 50 bp. This cloning vector is similar to pMT19, constructed by Hollifield, et al. (1987).

EXAMPLE 6

Addition of Synthetic T7 Promoter and Genome 5'-End Sequences

A modification of the technique of Kunkel (1985) for high efficiency site-directed mutagenesis (J. M. Polo and R. E. Johnston, unpublished results) was exploited in cloning the 5'- end of the VEE genome downstream of the T7 promoter. Comparison of sequence data from VEE genomic RNA and the upstream (5'with respect to virion RNA) terminus of cDNA clone 71-12 showed that the cDNA insert lacked nine nucleotides from the 5'-end of the VEE genome. E. coli* CJ236 ($dut^-$, $ung^-$) cells were transformed with 71-12 plasmid DNA. Single-stranded uridine-containing 71-12 DNA was rescued from the CJ236 transformants by superinfection with the defective helper phage M13K07 (Vieira and Messing, 1988). A 50-nucleotide primer was synthesized which included (from 5'to 3') 12 nucleotides complementary to the multiple cloning region of pUC118, including two G residues of the Sma I site, the untranscribed portion of the T7 promoter sequence (Rosa, 1980), an intervening G residue at the +1 position of the transcript, 8 nucleotides representing the VEE genome 5'-end, followed by 12 nucleotides complementary to the remaining G of the Sma I site and the upstream terminus of the viral sequence insert of clone 71-12 (FIG. 2). An estimated 40-fold molar excess of the phosphorylated 50-mer was annealed to single-stranded uridine-containing 71-12 DNA and extended in vitro with Klenow enzyme in the presence of T4 DNA ligase. Transformation of E. coli JM101 with the reaction mixture produced ampicillin- resistant colonies for further analysis. The initial screen was for reduced migration rate in agarose gel of the upstream terminal Sac I-Hind III fragment of 71-12 (approximately 600 bp). Two of 12 clones tested gave Sac I- Hind III fragments which ran detectably slower than the control fragment from the parent clone, 71-12. These candidate clones were tested for the correct sequence insertion and for T7 promoter activity as described below.

EXAMPLE 7

In Vitro Transcription and Transfection of Chicken Embryo Fibroblasts

Plasmid DNA was linearized by digestion with Not I, or another appropriate restriction enzyme, for use as a template in run-off transcription reactions. Following phenol-chloroform and ether extractions, template DNA was transcribed essentially as described by Rice et al., (1987), except that the reaction mixture contained 10 mM NaCl, and T7 RNA polymerase rather than SP6 RNA polymerase. A portion of the transcription reaction was diluted with buffer containing 10 mM Tris-HCl, pH 7.5, 10 mM EDTA, and 1% (w/v) SDS, heated for two minutes at 70C, and mixed with one-half volume of gel loading buffer (0.125% bromophenol blue in 50% glycerol). Electrophoresis through 0.8% agarose gel, made with sterile TBE (0.089M Tris-borate, 0.089M boric acid, 0.002M EDTA) containing 0.1% SDS, was followed by staining with ethidium bromide. When required, DNA templates were removed by addition of one unit of HPLC-purified DNase I (Pharmacia) to the transcription reaction and incubation for 10 min at 37C either before adding polymerase, or after the standard transcription reaction was complete. For digestion of RNA products, 1 mg/ml RNase A, prepared by boiling for 15 min, was added after the completion of transcription, and incubation was continued for 10 min at 37C. For transfection of CEF, transcription reactions were diluted in phosphate-buffered saline lacking Ca++and Mg++and applied to secondary monolayer cultures exactly as described by Polo et al. (1988).

EXAMPLE 8

Immunofluorescence

Indirect immunofluorescence assays were used for the detection of VEE antigens in RNA-transfected CEF. DEAE dextran-treated monolayers were exposed to transcription reaction mixtures or appropriate control mixtures, and incubated for 36 hours at 37C. The monolayers were then dispersed in trypsin, and the cells were washed in phosphate-buffered saline (PBS), air-dried on teflon-masked slides, and fixed in acetone at −20C. VEE- specific hyperimmune mouse ascitic fluid (HMAF), prepared by the method of Brandt et al. (1969), or an El-specific monoclonal antibody (PTF-39-1A4A-1) provided by Dr. J. Roehrig, were diluted in PBS and used as primary antibodies. Following washing in PBS, the slides were reacted with an affinity-purified fluorescein-conjugated, goat anti-mouse IgG for 30 minutes, washed in PBS, and mounted in carbonate-buffered glycerol containing 1 mg/ml p-phenylenediamine. Positive controls, consisting of transfections with Totol101 transcripts, were monitored with a direct fluorescein conjugate produced from the IgG fraction of HMAF directed against western equine encephalitis virus.

EXAMPLE 9

Synthesis and Characterization of a VEE cDNA Library

VEE cDNAs were cloned using the same procedures that were successful in producing a cDNA library that represented all but the 15 5'-terminal nucleotides of the Sindbis virus genome (Polo et al., 1988). From more than 600 clones containing VEE-specific sequences, 76 clones with inserts ranging in size from 1.5 to over 5 kbp were selected for further study. The clones were ordered with respect to one another and with respect to restriction sites predicted from the published sequence of the 3'-one third of the VEE genome (Kinney et al., 1986). This was accomplished using single and double restriction digests with pairs of enzymes whose sites flank the Sma I site in the multiple cloning region. Analysis of sequence data obtained from the cDNA clones and comparisons with the published sequence verified these preliminary groupings and produced the final arrangement of selected clones shown in FIG. 1.

Interestingly, the downstream (3'with respect to virion RNA) sequences of clones 3-23, 3-31 and 55-21 included terminal oligo (A) tracts ranging in length from 14 to 20 nucleotides (FIG. 1), which suggests that these clones were produced by internal priming of first strand synthesis with oligo d(T). Sequencing with the Vll primer on the group 2 clones revealed a region of the VEE genomic sequence in which A residues constituted 11 of 14 nucleotides (virion-sense). This A-rich region in Group 2 clones exactly overlapped the oligo (A) tracts in the Group 3 clones. Therefore, it appears likely that one mechanism for synthesis of cDNAs which do not contain the 3'-end of the genome is internal priming by oligo d(T) on A-rich sequences.

The estimated total length of the cloned sequence was over 11 kb, suggesting that only a small portion of the 5'-end of the genome was not represented. In fact, upstream terminal sequences of clones 24-20 and 71-12, when compared to the partial 5'-terminal sequence of VEE determined previously by an enzymatic method (Ou, et al., 1983), appeared to include all but 13 nucleotides or 9 nucleotides, respectively, of the genome 5'-end (FIG. 3). To confirm this, the 5'-end sequence was determined for the RNA of this isolate of VEE. RNA sequencing reactions with the V12 primer (labeled arrow in FIG. 1) on VEE virion RNA produced two "strong stops" at a distance of 22 and 23 nucleotides from the 3'-end of the primer. The sequence obtained was consistent with that published by Ou, et al. for VEE (1983, FIG. 3). The specific nucleotides at positions 22 and 23 were obscured by the strong stops, which may have been caused by steric hindrance of reverse transcriptase by the methylated cap, but were assumed to be m7G(5')ppp(5')A as reported previously. The published sequence of the 5'-end, and the sequence obtained directly from the RNA, and the overlapping sequences obtained from the termini of clones 24-20 and 71-12 together constitute the 5'-terminal 175 nucleotides of the VEE genome (FIG. 3). The methylated cap plus 44 nucleotides are followed by an AUG codon in a preferred context for initiation of translation (Kozak, 1981). The deduced amino acid sequence of the predicted protein (FIG. 3) shows extensive homology to that predicted for the N-terminus of Sindbis virus nsP1 protein (Strauss et al., 1984).

The data described above provide strong evidence that the 20 cDNA clones diagrammed in FIG. 1 together represent all but the 9 nucleotides at the exact 5'-end of the VEE genome. The clones were analyzed further with a combination of single and double restriction digests using additional enzymes. Recognition sites for a total of 19 restriction enzymes were mapped in the cloned sequence (FIG. 1). Distances between restriction enzyme sites in the nonstructural gene region are approximations based on relative migration rates of fragments in agarose gels. Eight of the 19 enzymes appeared to cut at unique sites in the genomic sequence. Unique sites were confirmed for five of these, either by searching the published sequence of the 26S region (Sph I, Sac II, Afl II) or by sequencing of clone termini (Sal I, BssH II). Based on restriction digest results, the three remaining enzymes (Eco RI, Xho I, Tth III 1) might recognize unique sites or multiple closely spaced sites.

For the enzymes used in this study, all of the sites predicted from the published 26S sequence were present, except for one Eco RI site in the capsid gene. This polymorphism may reflect the fact that different laboratory stocks of VEE were used for sequencing (Kinney et al., 1986) and for generating these cDNA clones. One enzyme, Xba I, cut at the predicted site in the E2 gene [labeled (X) in FIG. 1]only when the DNA substrate was isolated from the nonmethylating strain *E. coli* GM33. It is probable that the sequence in this region (GAmTCTAGA) signals methylation of the A residue directly upstream of the recognition sequence, thereby blocking enzyme activity. This partial map of restriction enzyme cleavage sites guided the construction of a candidate full-length VEE clone using selected members of the cDNA library.

EXAMPLE 10

Construction of a Candidate Full-Length VEE cDNA Clone Downstream From a T7 Promoter The first step in construction of a full-length cDNA clone was to design a cloning vector which could accomodate an 11-12 kbp insert. The pTX plasmid was made by joining the pBR322- derived sequences from the full-length Sindbis cDNA clone, Toto1101 (Rice et al., 1987), to the multiple cloning region from pUC118 as described above.

The placement of the exact 5'-end of the VEE genome downstream from a synthetic T7 promoter was accomplished by using techniques of in vitro mutagenesis to insert a 26-nucleotide sequence at the appropriate position in VEE cDNA clone 71-12 (see above). The altered 71-12 clone, pT7 71-12, when tested in run-off transcription assays, gave transcripts of the expected length in amounts comparable to the amount of RNA transcribed from a Bluescript cloning vector BSKS+ (Stratagene). Sequence analysis of clone pT7 71-12 showed that the T7 promoter, an intervening G residue and the 9 nucleotides of the VEE genome 5'-end had been correctly inserted into clone 71-12 (data not shown). These results established that the synthetic T7 promoter sequence, although different from the consensus promoter (Rosa, 1980), gave normal levels of transcription.

Detectable amounts of infectious Sindbis virus RNA are obtained by transcription of supercoiled Toto1101 DNA templates. However, the proportion of genome-length transcripts from Toto1101 is greatly increased if, prior to transcription, the plasmid is digested at a unique Xho I site just downstream of the Sindbis virus poly (A) tract (Rice et al., 1987). An analogous unique site was not present in the VEE cDNA clones. However, the restriction enzyme Not I failed to cleave any cloned VEE sequence tested. Therefore, a Not I site was inserted in place of the Kpn I site downstream of the $(A)_{21}$ tract in clone 67-12 (FIG. 1) using standard techniques (Maniatis et al., 1982; Ausubel et al., 1987). The altered clone, 67-12(N), was no longer a substrate for Kpn I, but had a unique Not I site at the expected position. The alteration was confirmed by sequencing (data not shown).

Figure 4:
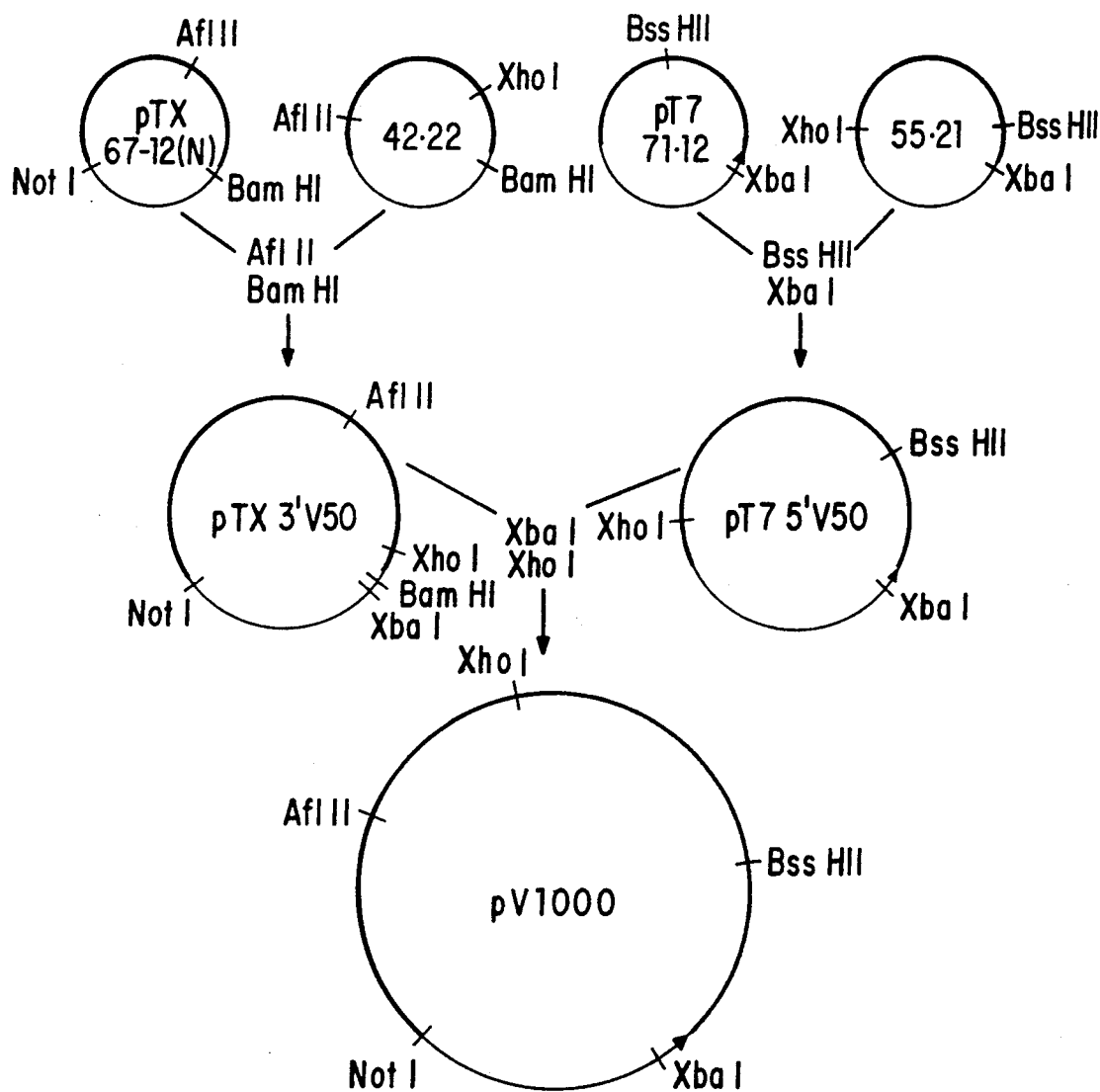
FIG. 4. Scheme for construction of a candidate full-length cDNA clone of VEE downstream from a T7 promoter. Procedures for the construction of pTX 67-12(N) and pT7 71-12 are described in the examples. The T7 promoter (arrow) is adjacent to the VEE genome 5'-end. The (A)$_{21}$ tract in clone pTx 67-12(N) is adjacent to the unique Not I site. Bold arcs describe viral cDNA inserts. The approximate positions of restriction sites are marked.
Figure 6B:
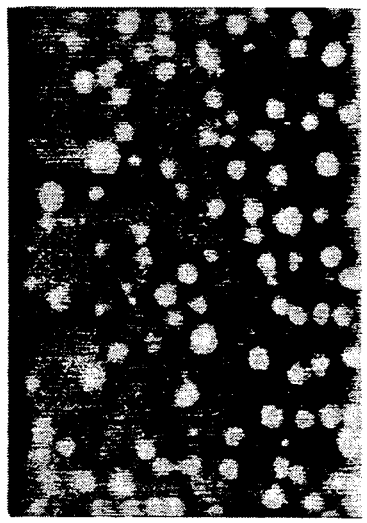
FIG. 6A-D. VEE antigens detected in RNA-transfected CEF by indirect immunofluorescence. Acetone-fixed cells from treated cultures were reacted with VEE-specific hyperimmune mouse ascites fluid (HMAF) and subsequently with an affinity purified, goat anti-mouse IgG fluorescein-conjugate. A. Cells treated with PBS (buffer control). B. Cells transfected with untranscribed, Not I-digested pV1000 DNA. C. Cells transfected with purified VEE virion RNA. D. Cells transfected with pV1000 DNA transcription reaction mixture.
Figure 6D:
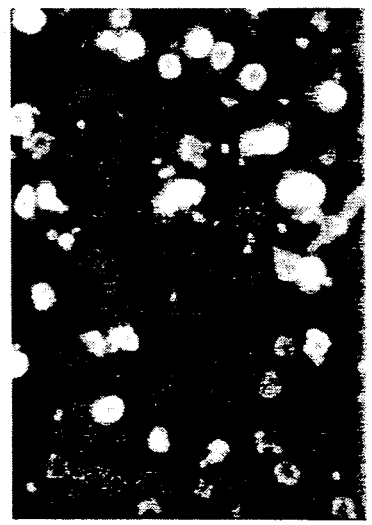
Figure 6A:
Figure 6C:

It remained to join appropriate restriction fragments from the transcribing 5'-end clone, pT7 71-12, the suitably altered 3'-end clone, 67-12(N), and clones containing intervening viral sequences and insert them into the pTX vector. This was accomplished in several steps as diagrammed in FIG. 4. All constructs were verified by single and double restriction enzyme digests. First, clone 67-12(N) and pTX were digested with Eco RI and Bam HI, and the appropriate fragments were gel-purified and joined to give pTX 67-I2(N). Next, Afl II and Bam HI were used in double digests of pTX 67-12(N) and clone 42-22 (FIG. 1). The appropriate fragments were gel purified and joined, giving pTX 3'V50. The 5'-half of the genome was constructed in pUC118 by digesting clone pT7 71-12 and clone 55-21 (FIG. 1) with Xba I and BssH II and joining the appropriate gel-purified fragments. pT7 5'V50 showed undiminished T7 promoter activity compared to clone pT7 71-12, and when linearized at various restriction sites for run-off transcription, gave transcripts of the expected relative lengths (data not shown). The final step in construction of the candidate full-length clone in pTX was ligation of appropriate Xba I- Xho I fragments from pT7 5'V50 and pTX 3'V50.

EXAMPLE 11

Characterization of Candidate Full-Length VEE cDNA Clones

The initial screen of candidate full-length clones was digestion of plasmid DNA with Hind III. The map of restriction enzyme sites (FIG. 1), in conjunction with the known orientation of cloned inserts, predicted that the overlapping Hind III fragments of pT7 5'V50 and pTX 3'V50 (5.2 kbp and 2.1 kbp, respectively) would be replaced by a single fragment of approximately 3.3 kbp spanning the Xho I junction site in a full-length clone. Seven of 12 ampicillin-resistant transformants carried plasmids with the expected pattern (data not shown). DNA preparations from three of these clones, pV1000, pV1001 and pV1002, were analyzed by digestion with additional restriction enzymes to verify the construction.

DNA samples from pV1000, pV1001, and pV1002 were linearized with Not I, purified and used as templates in parallel T7 transcription reactions. Portions of the transcription reaction mixtures were analyzed by electrophoresis through an agarose gel followed by staining with ethidium bromide. All three transcription reactions showed a band corresponding to the linearized template DNA and an additional band with the migration rate expected for VEE genome RNA (data not shown). Portions of the transcription mixtures also were applied to CEF monolayers which had been treated with DEAE-dextran. Monolayers treated with each of the three transcription mixtures showed cytopathic effect (CPE) at 36 hours after transfection. The degree of CPE was comparable to that shown by control monolayers treated with 0.3 ug of purified VEE virion RNA or with a Totol101 transcription mixture (data not shown). Transfection with the untranscribed, linearized DNA template did not produce CPE. Clones pV1000, pV1001 and pV1002 were considered to be identical based on the above results, and in the following experiments were used interchangeably.

A replicate of these clones designated pV1003 was deposited in *Escherichia coli* strain HB101 at the American Type Culture Collection in Rockville, Maryland, USA, in accordance with the Budapest Convention, on Jun. 16, 1989, and given ATCC Accession Number 68013.

Figure 5:
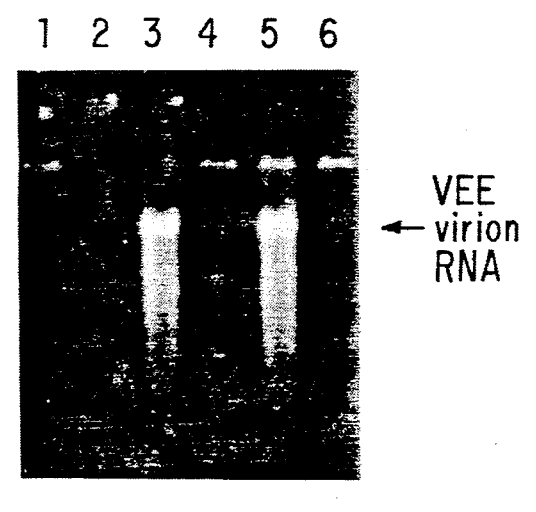

The effects of nuclease treatment and temperature on the synthesis of infectious RNA in vitro are described in FIG. 5 and Table 1. The DNA template was treated with DNase I either before or after incubation with T7 RNA polymerase. In the first case, neither the template band nor the virion RNA-length band appeared in the gel, and no infectivity was detected in the transcription reaction mix. In the second case, the template band was not present, but the virion RNA-length band and infectivity were detected. Treatment of the reaction mixture with RNase A following transcription eliminated the viroin RNA-length band as well as the infectivity. A significantly lower, but still detectable, amount of infectious RNA was made at 4C. When monolayers transfected with 2.5-3.2 ug of in vitro transcripts (based on comparative staining with ethidium bromide) were compared to cultures transfected with 0.3 ug of VEE virion RNA, the appearance of CPE induced by the RNA synthesized in vitro was comparable to that induced by virion RNA.

TABLE 1

Nuclease and Temperature Sensitivity of In Vitro Transcription

| Condition[a] | CPE at 16 hr | PFU/ml of culture medium at 16 hr[b] | Supernatant infectivity for BHK cells[c] |
|---|---|---|---|
| DNase I before transcription | — | $<10^{2.d}$ | — |
| DNase I after transcription | + | $1.32 \times 10^7$ | + |
| RNase A after transcription | — | $<10^{2.d}$ | — |
| Complete, untreated | + | $1.75 \times 10^7$ | + |
| Complete, 4C incubation | — | $5.1 \times 10^6$ | + |

[a]Complete reactions were constituted and nuclease treatments carried out as described in Materials and Methods. One half of each 10-ul transcription reaction was diluted with PBSD for application to DEAE-dextran-treated CEF.
[b]Supernatants of transfected cultures were sampled at 16 hr post-transfection for assay of plaque-forming units on Vero cell monolayers using standard procedures.
[c]Supernatants of transfected cultures were collected at 16 hr post-transfection and transferred to uninfected BHK cell monolayers. These monolayers were scored for CPE after 16 hr.
[d]No plaques detected in a 1:100 dilution.

CEF monolayers treated with various transcription reaction mixtures were analyzed for the presence of viral antigens by indirect immunofluorescence (Table 2 and FIG. 6). Under the conditions used, VEE antigens were detected with both polyclonal and monoclonal anti-VEE antibodies in CEF treated with purified VEE virion RNA or with transcription products of pV1000, pV1001 and pV1002 cDNA clones (data for pV1001 and pV1002 were equivalent to those shown for pV1000). Cultures treated with untranscribed pV1000 DNA were negative in immunofluorescence assays. Polyclonal anti-VEE antibody showed only a faint cross reaction with cells receiving Totol101 transcription products, and the monoclonal anti-VEE antibody was unreactive. Conversely, antibody raised against western equine encephalitis virus, which strongly cross-reacts with Sindbis virus (Porterfield, 1980), bound to the Totol101-treated cells, but showed only minimal binding to cultures that received pV1000, pV1001 and pV1002 transcription mixtures.

TABLE 2

Binding of anti-VEE and anti-western equine encephalitis virus (WEE) antibodies to RNA-transfected CEF[a]

| | Cells reacted with: | | |
|---|---|---|---|
| Cells transfected with: | Anti-VEE monoclonal antibody | Anti-VEE polyclonal HMAF[b] | Anti-WEE polyclonal HMAF |
| PBS buffer | — | — | — |
| Untranscribed pV1000 DNA | — | — | — |
| VEE virion RNA | ++ | ++++ | + |
| Totol101 transcripts | — | ++ | ++++ |
| pV1000 transcripts | ++++ | ++++ | + |

[a]Chick embryo fibroblasts (CEF) treated as described in FIG. 7.
[b]HMAF, hyperimmune mouse ascites fluid.

To show that the cells displaying VEE antigens were also producing infectious progeny virions, culture supernatants were removed from CEF monolayers transfected with pV1000, pV1001 and pV1002 transcripts and transferred to uninfected BHD cell mono layers. The BHK cell cultures showed significant CPE within 36 hours and the culture supernatants contained plaque-forming units, as assayed on Vero cells. No differences were detected between the growth of virus derived from clones pV1000, pV1001 and pV1002 and the growth of the parental VEE in any of these cell types.

EXAMPLE 12

Sequence Analysis of pV1002

The results described above indicated that full-length cDNA clones had been constructed and that these candidate full-length clones could be transcribed in vitro to give infectious VEE RNA. However, digestion of these clones with Sac I indicated that one predicted Sac I site was not present (data not shown). Double digests with Sac I and Xho I identified the missing Sac I site as the one which had been mapped very near the Xho I site (refer to FIG. 1). In contrast, clones pT7 5'V50 and pTX 3'V50, which were the source of DNA fragments used in the construction, did contain all of the predicted Sac I sites. Taken together, these results indicated that: 1) multiple closely-spaced Xho I sites flanking a Sac I site were present in the VEE genome sequence, and 2) sequences between the most 5'and most 3'Xho I sites, including the Sac I site, had been deleted from the clone.

cDNA clones pV1000, pV1001 and pV1002 lacked a portion of the VEE genome sequence, and yet RNA transcribed from these clones was infectious. It was of interest, therefore, to determine the nature of the deletion at the nucleotide sequence level. Dideoxynucleotide sequencing with primer V13 (labeled arrow in FIG. 1) was performed using VEE virion RNA and clone 3-31 single-stranded DNA as templates to determine the parental VEE sequence in the region of the deletion. Single-stranded M13 DNA containing the subcloned 3.3 kbp Hind III "junction" fragment of pV1002 and RNA purified from pV1002 progeny virions were sequenced to identify the extent of the deletion. The results are shown in FIG. 7. The VEE genome sequence (FIG. 7A, 7B) contains three Xho I sites (CTCGAG) in this region; the central Xho I site overlaps a Sac I site (GAGCTC). pV1002 (FIG. 7C and 7D) was formed by deletion of 102 nucleotides when the most 5'and most 3'Xho I sites were joined in the final step of construction.

The VEE genome sequence in the region of the deletion was part of a long open reading frame assumed to be the one that is used in translation (FIG. 8). Sufficient homologies in predicted amino acid sequence were found between VEE and other alphaviruses (Strauss et al., 1984; Takkinin, 1986; Faragher et al., 1988) to locate the deletion at the extreme 3'-end of the nsP3 gene. The predicted amino acid sequence is interrupted by an opal stop codon separated by five codons from a gly X/tyr consensus cleavage site (Strauss et al., 1987). Downstream from the consensus cleavage site, the VEE sequence exhibited a high degree of homology with Sindbis virus nsP4. The 102 nucleotide deletion removed 34 codons from the predicted translation product while maintaining the same reading frame.

Figure 9A:
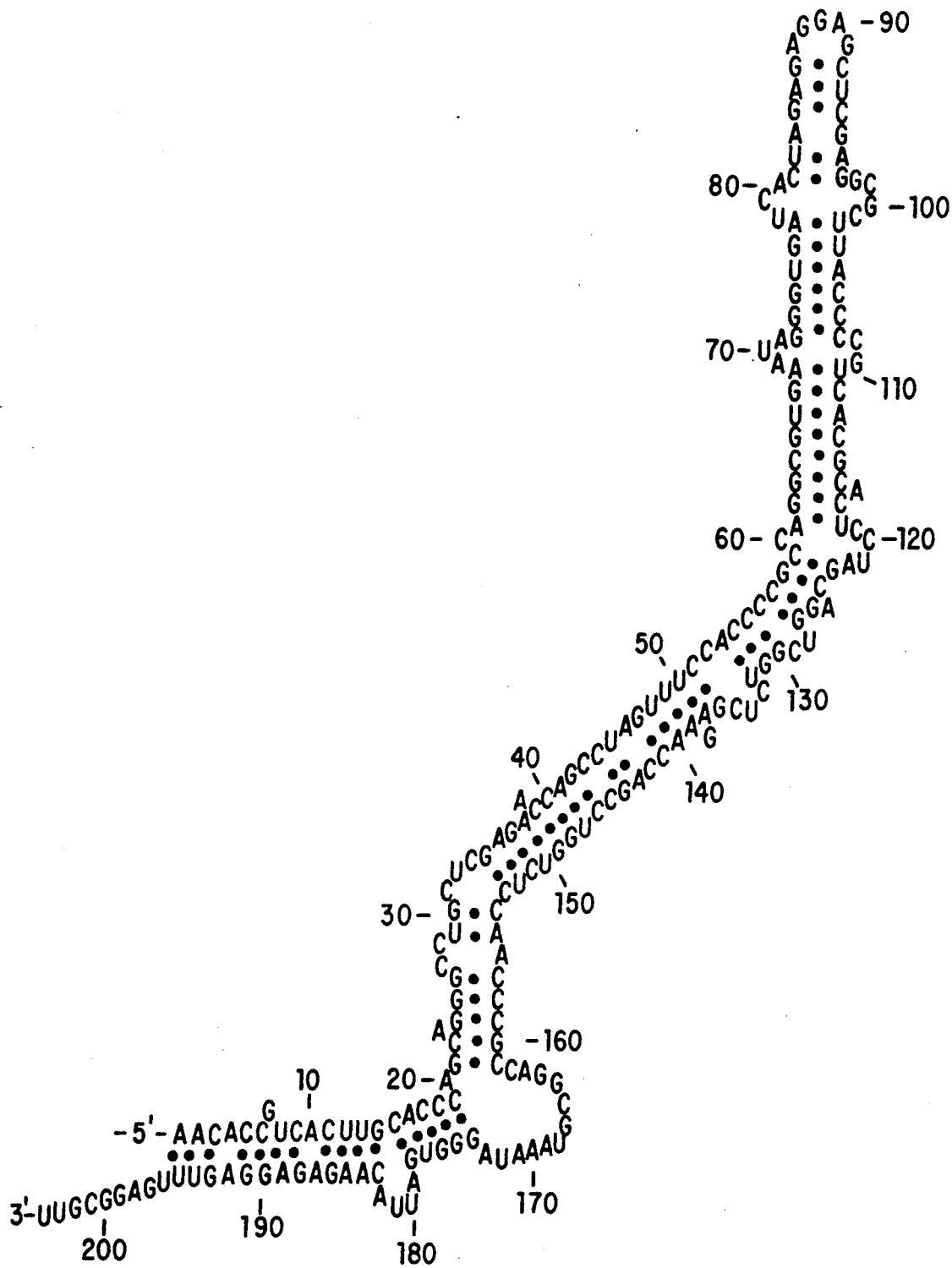
FIG. 9A-B. Predicted RNA secondary structures in the region of the pV1002 deletion. A. Secondary structure predicted for the two tandem repeats in the VEE genomic sequence. B. Secondary structure predicted for the sequence found in RNA transcripts of the cDNA clone pV1002.
Figure 9B:
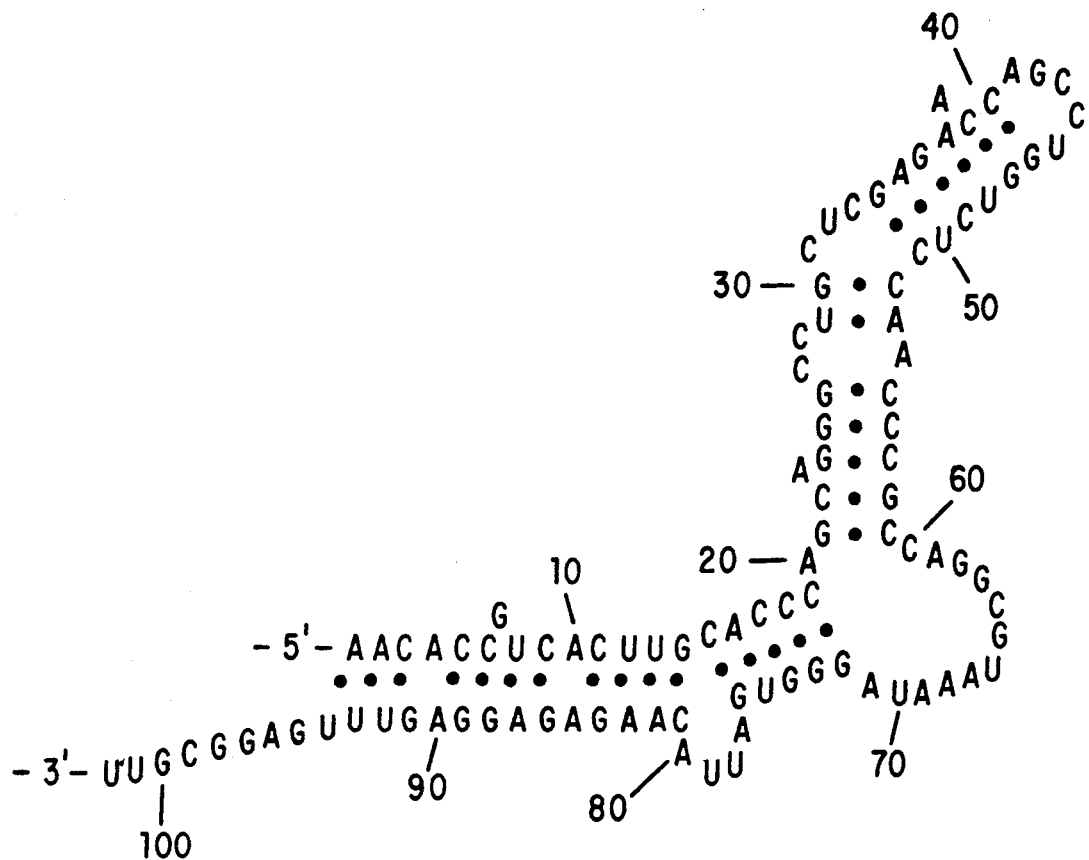

Examination of the deleted sequence and flanking regions revealed the presence of two 102 nucleotide tandem repeats ending 16 nucleotides upstream from the opal stop codon (FIG. 8). The two tandem units were not exact repeats. Comparison of the two repeat units with each other showed 20 nucleotide differences which resulted in 6 amino acid coding changes. Computer assisted secondary structure analysis (Zuker and Stiegler, 1981) predicted that a large and stable stem-loop structure could be formed by intramolecular hydrogen bonding between elements of the two repeat units (FIG. 9A). The non-lethal deletion in pV1002 joined the 5' 31 nucleotides of the first repeat with the 3' 71 nucleotides of the second repeat, conserving a single copy of the repeat at both the nucleotide and amino acid levels. The effect of the deletion on the predicted secondary structure also was remarkably conservative as illustrated in FIG. 9B.

DISCUSSION OF EXAMPLES 1-12

In this report we describe a cDNA clone derived from the genome of VEE that can serve as a template for transcription of infectious VEE RNA. The construction of the genomic clone involved three main steps. Initially, a library of cDNA clones including all but the 5'-terminal nine nucleotides of the Viral genome was generated. Secondly, a synthetic T7 promoter and the nine nucleotides of the genome 5'-end were added to the cloned sequence by in vitro mutagenesis. Finally, linkage of viral sequences from four clones resulted in pV1000, a cDNA clone in a transcription vector that was predicted to contain the complete VEE genome sequence.

Three types of evidence confirmed that in vitro transcripts of the candidate VEE genomic clone were infectious. First, cells transfected with in vitro transcripts of the VEE genomic clone demonstrated cytopathic changes consistent with VEE infection and expressed VEE antigens as shown by immunofluorescence. Furthermore, the culture media from the same transfected cells could be used to propagate the infection in fresh cells. Therefore, transfection with in vitro transcripts of the genomic clone initiated a productive VEE infection. Second, DNase I digestion of the DNA template before transcription, or RNase A digestion of the RNA transcripts, completely destroyed the infectivity of the transcription reaction mixture, showing that the infectivity of the mixture resided in the RNA transcript of the intact cloned sequence. Third, formal proof that progeny virions indeed resulted from the RNA transcripts came from sequence analysis of the VEE genomic clone and RNA isolated from progeny virions. Both showed an identical 102 base deletion.

We considered three parameters in designing a strategy for construction of a full-length cDNA clone in a transcription vector. One was the fact that the cloning vector had to accomodate an 11-12 kbp insert. As expected, the 1898 bp modified pBR322 vector sequence from the Sindbis virus cDNA clone, Toto1101 (Rice et al.,1987), formed a stable plasmid when linked to the 11-12 kbp insert of pV1000. Next, the efficiency of transcription had to be sufficiently high to allow detection of infectious RNA. In vitro studies of T7 RNA polymerase activity predicted that the nucleotides GAU at the beginning of the transcribed sequence would be part of an efficient T7 promoter (Milligan et al., 1987). Lastly, the structure of the 5'-end of the transcript would be important both for efficiency of translation of viral nonstructural proteins and for recognition by virus-specific replication complexes. Previous studies with Toto1101 have shown that alphavirus replication complexes may accomodate a small number of extra nucleotides at the 5'-end, and that capped transcripts are 100-fold more infectious than uncapped transcripts (Rice et al., 1987).

The final structure of pV1000 included a T7 promoter with the sequence GAU in the +1, +2 and +3 positions of the transcript, in which A represented the exact 5'-end of the authentic VEE genome sequence. The cap analog m7G(5')ppp(5')G was included in the transcription reaction as described previously (Nielsen and Shapiro, 1986). Agarose gel analysis of transcripts indicated that the level of transcription from this promoter was comparable to that from the T7 promoter of the Bluescript cloning vector. The in vitro transcripts are assumed to initiate with the sequence m7G(5,)ppp(5,)GAU, and to have a 5,-end identical to that of the VEE genome except for a single extra G.

Characterization of pV1000 revealed that it lacks 102 nucleotides of VEE genomic sequence. In spite of this fact, transcripts of pV1000 can initiate a productive VEE infection. One possible explanation for this result is that a second compensating mutation occurred during synthesis of either the cDNA or the RNA transcripts. Only a comparison of the complete genomic sequences of the progeny and parental VEE viruses would prove or disprove the existence of such a mutation. However, the observations described in this paper lend support to the alternative hypothesis that the deleted sequence simply may not be required for virus replication in CEF, BHK or Vero cells. Multiple candidate clones reproducibly gave infectious transcripts, and the rate of appearance of CPE and progeny virus in transfected cultures indicated that a significant proportion of the in vitro transcripts were infectious. Preliminary results indicate that the deletion mutant also is able to replicate in the mouse (J. Smith, N. Pesik, N. Davis, L. Willis and R. Johnston, unpublished results). Future studies of this mutant will be directed toward defining possible phenotypic effects of the deletion.

Sequence analysis in the region flanking the deletion, and comparison to known alphavirus sequences (Strauss et al., 1984; Takkinin, 1986; Faragher et al., 1988), placed the deleted sequence at the 3'-end of the nsP3 gene. This portion of the nsP3 sequence is not conserved among the alphavirus genomes which have been analyzed. The extreme case is Middelburg virus, which lacks 88 codons that are present at the 3'-end of the Sindbis nsP3 gene (Strauss and Strauss, 1986). The Sindbis virus and Semliki Forest virus nsP3 proteins have been shown to be phosphoproteins (Peranen et al., 1988; G. Li and C. M. Rice, personal communication). The VEE nsP3 protein may also be a substrate for phosphorylation, since serine and threonine constitute 24% of the 82 predicted amino acid residues at the carboxy-terminal end of the VEE nsP3 protein described in this report. The role of phosphorylation in nsP3 function and/or stability is not yet known.

The deletion in pV1002 occurred within a region containing two somewhat divergent sequence repeat units in tandem. Presumably, these repeated elements arose by a 102 base sequence duplication. Subsequent evolutionary divergence would have resulted in the sequence differences evident between the two elements at both the nucleotide and amino acid levels. Much shorter repeats at the amino acid level have been observed previously in the predicted carboxy termini of Sindbis, Ross River and Semliki Forest virus nsP3 proteins (Takkinin, 1986; Faragher et al., 1988).

The possible importance of the repeats at the nucleotide level is suggested by the prediction of a large stem-loop structure formed by intramolecular hydrogen bonding between the two repeat units and the conservation of a considerable portion of that structure in the viable deletion mutant pV1002. If one assumes that the first repeat unit was the primordial sequence, then 12 of the 20 nucleotide differences in the second repeat would strengthen the predicted structure and 8 would have no effect. If one assumes that the second repeat was the primordial sequence, then 15 of 20 differences in the first repeat unit would strengthen, 4 would have no effect and 1 would weaken the structure. While it is highly probable that neither repeat unit reflects the original sequence at the time of the duplication, this sort of analysis suggests that the RNA secondary structure of this region is important in an evolutionary sense. However, alphavirus RNAs are noted for their generally high degree of secondary structure (Sreevalsan et al., 1968). We have observed that a number of sequences of similar size, selected at random from the Sindbis genomic sequence, were predicted to form stem-loop structures as large and as stable as that predicted for the VEE region analysed here. Additional information as to the function of this region must await directed mutagenesis experiments which alter or eliminate these sequences from the VEE clone.

Sequence analysis in the region of the pV1000 deletion also identified VEE as an alphavirus which carries an opal codon between its nsP3 and nsP4 genes. This places VEE in the group including Sindbis virus, Middelburg virus and Ross River virus, all of which possess an opal codon at this position (Strauss et al., 1987). In addition, the sequence data predict a consensus proteolytic processing site beginning five codons from the opal stop codon. The gly-ala-tyr sequence is identical to that found for both Middelburg virus and Ross River virus. Sequence data obtained during the construction of the cDNA clone include the 5'-terminal 175 nucleotides of the VEE genome, and extend the partial, enzymatically determined 5'-end sequence published previously (Ou et al., 1983). It has been suggested that four distinct sequence elements may be involved in the control of alphavirus RNA replication (Ou et al., 1983), although one of them does not appear to be necessary for replication or packaging of defective-interfering particle RNA (Levis et al., 1986). The identification of these regions depended primarily on analysis of homologous sequences among different alphaviruses. Two of these homologous sequence elements near the 5'-terminus were also found in VEE. For example, a conserved sequence represented by nucleotides 1 - 44 of the Sindbis virus genome (HR small plaque strain, Strauss et al., 1984) can be arranged in a stable stem and loop structure. The nucleotides which form the stem are largely conserved in the VEE genome 5,-terminus, while residues in the loop are not. Thus the VEE sequence can be arranged to give a similar stem but a smaller loop with only a small loss of stability. In addition, the portion of the SB-HR 51-nucleotide conserved sequence that includes nucleotides 155 through 193 (Ou et al., 1983) was also found, with only 5 nucleotide changes, in the VEE sequence spanning nucleotides 134-173. The predicted secondary structure for the VEE sequence in this region is similar to those predicted for other alphaviruses (Ou et al., 1983). Our findings add support to the hypothesis that these sequences, possibly through secondary structures in which they are involved, perform some cis-acting function in the alphavirus life cycle.

EXAMPLE 13

Identification of Attenuating Mutations

The construction of an infectious clone of VEE represents the starting point for a series of studies involving directed mutagenesis of the VEE genome. The scope of these experiments, as has been true of those with the Sindbis virus infectious clone, will encompass all areas of VEE biology, epidemiology and pathogenesis. One use of this tool will be the development of new live virus vaccines for Venezuelan encephalitis using a unique molecular strategy. Distinct point mutations that attenuate the virulence of VEE in animal model systems are being identified by sequence analysis of mutants isolated previously (Johnston and Smith, 1988). These data are given in FIG. 10. At least one, more preferably at least two, and most preferably at least three such mutations, are then introduced together into the infectious clone to produce a multiply attenuated template for a more stable VEE vaccine strain.

The foregoing examples are illustrative of the present invention, and are not to be taken as restrictive thereof. The invention is defined by the following claims, with equivalents of the claims to be included therein.

That which is claimed is:

1. A DNA comprising a cDNA clone coding for an infectious Venezuelan Equine Encephalitis (VEE) Virus RNA transcript and a heterologous promoter positioned upstream from said cDNA clone and operatively associated therewith, and further comprising at least one attenuating mutation selected from the group consisting of codons at E2 amino acid position 76 which specify an attenuating amino acid and codons at E2 amino acid position 209 which specify an attenuating amino acid.

2. A DNA according to claim 1, wherein said attenuating mutation comprises a substitution mutation.

3. A DNA according to claim 2, wherein said substitution mutation codes for an amino acid selected from the group consisting of lysine, arginine, and histidine as E2 amino acid 76.

4. A DNA according to claim 2, wherein said substitution mutation codes for an amino acid selected from the group consisting of lysine, arginine, and histidine as E2 amino acid 209.

5. A DNA according to claim 1, further comprising an intervening G residue positioned between said cDNA clone and said heterologous promoter at the position where transcription initiates at the 5′ end of said cDNA clone.

* * * * *

UNITED STATES PATENT AND TRADEMARK OFFICE
CERTIFICATE OF CORRECTION

PATENT NO. : 5,185,440

DATED : February 9, 1993

INVENTOR(S) : Nancy L. Davis, Loretta V. Willis, Robert E. Johnston, and Jonathan F. Smith It is certified that error appears in the above-identified patent and that said Letters Patent is hereby corrected as shown below:

On the title page, item [54] and column 1, line 1, correct "CDNA" to read --cDNA--.

Column 3, Line 32, correct "17-527" to read -- 517-527 --.

Column 3, Line 62, correct "RaCaniello" to read -- Racaniello --.

Column 4, Line 33, correct "40-744" to read -- 740-744 --.

Column 4, Line 55, correct "809-3819" to read -- 3809-3819 --.

Column 4, Line 58, correct "47," to read -- 147, --.

Column 5, Line 32, correct "Vos, p," to read -- Vos, P, --.

Column 7, Line 22, correct "VI000" to read -- V1000 --.

Column 11, Line 38, correct " 3,-end" to read -- 3'-end --.

Column 12, Line 7, correct " pUCI18 " to read -- pUC118 --.

Column 12, Line 15, correct " [VII," to read -- [V11 --.

Column 18, Line 31, correct " BHD" to read -- BHK --.

Column 20, Line 43, correct " (5,)ppp(5,) GAU, and to have a 5,-end" to read -- (5')ppp(5') GAU, and to have a 5'-end --.

UNITED STATES PATENT AND TRADEMARK OFFICE
CERTIFICATE OF CORRECTION

PATENT NO. : 5,185,440

DATED : February 9, 1993

INVENTOR(S) : Nancy L. Davis, Loretta V. Willis, Robert E. Johnston, and Jonathan F. Smith It is certified that error appears in the above-identified patent and that said Letters Patent is hereby corrected as shown below:

Column 22, Line 15, correct " 5,-terminus," to read
-- 5'-terminus, --.

Signed and Sealed this

Twenty-third Day of November, 1993

BRUCE LEHMAN

Attesting Officer     Commissioner of Patents and Trademarks